US006368658B1

(12) United States Patent
Schwarz et al.

(10) Patent No.: US 6,368,658 B1
(45) Date of Patent: Apr. 9, 2002

(54) COATING MEDICAL DEVICES USING AIR SUSPENSION

(75) Inventors: Marlene Schwarz, Newton; Kathleen Miller, Shrewsbury; Kalpana Kamath, Natick, all of MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/551,614

(22) Filed: Apr. 17, 2000

Related U.S. Application Data

(63) Continuation-in-part of application No. 09/293,994, filed on Apr. 19, 1999, now abandoned.

(51) Int. Cl.[7] .............................................. B01J 13/00
(52) U.S. Cl. .................... 427/2.15; 427/2.24; 427/2.25; 427/2.28; 427/2.3; 427/457; 427/458; 427/459; 427/466; 427/523; 427/581; 427/582; 427/585; 427/496; 427/488; 427/595; 427/596; 427/248.1; 427/255.5; 427/255.6
(58) Field of Search ............................. 427/2.24, 2.25, 427/2.28, 2.3, 2.15, 313, 5, 6, 457, 458, 459, 460, 523, 581, 582, 585, 496, 488, 595, 596, 248.1, 255.5, 255.6; 118/309, DIG. 5

(56) References Cited

U.S. PATENT DOCUMENTS

| | | | |
|---|---|---|---|
| 2,648,609 A | | 8/1953 | Wurster ........................ 99/116 |
| 2,799,241 A | | 7/1957 | Wurster ........................ 118/24 |
| 3,089,824 A | | 5/1963 | Wurster ........................ 167/82 |
| 3,253,944 A | | 5/1966 | Wurster ........................ 117/100 |
| 3,567,485 A | * | 3/1971 | Lemelson ...................... 117/21 |
| 4,000,338 A | | 12/1976 | Burdin .......................... 427/184 |
| 4,180,560 A | | 12/1979 | Katz et al. ..................... 424/21 |
| 4,320,089 A | * | 3/1982 | Huttlin ......................... 422/140 |
| 4,349,498 A | * | 9/1982 | Ellis et al. ..................... 264/81 |
| 4,428,973 A | * | 1/1984 | Horner et al. ................. 427/3 |
| 4,432,933 A | * | 2/1984 | Teitel et al. ................... 376/152 |
| 4,529,614 A | | 7/1985 | Burns ........................... 427/2 |
| 4,535,006 A | | 8/1985 | Naunapper et al. ........... 427/213 |
| 4,592,920 A | | 6/1986 | Murtfeldt ....................... 427/2 |
| 4,666,704 A | | 5/1987 | Shalati et al. .................. 424/19 |

(List continued on next page.)

FOREIGN PATENT DOCUMENTS

| | | |
|---|---|---|
| DE | 33 23 418 | 1/1985 |
| WO | WO96/17692 | 6/1996 |

*Primary Examiner*—Fred J. Parker
*Assistant Examiner*—Jennifer Kolb Michener
(74) *Attorney, Agent, or Firm*—Kenyon & Kenyon

(57) ABSTRACT

Methods and apparatuses for coating medical devices and the devices thereby produced are disclosed. In one embodiment, the invention includes a method comprising the steps of suspending the medical device in an air stream and introducing a coating material into the air stream such that the coating material is dispersed therein and coats at least a portion of the medical device. In another embodiment, the medical devices are suspended in an air stream and a coating apparatus coats at least a portion of the medical device with a coating material. The coating apparatus may include a device that utilizes any number of alternative coating techniques for coating the medical devices. This process is used to apply one or more coating materials, simultaneously or in sequence. In certain embodiments of the invention, the coating materials include therapeutic agents, polymers, sugars, waxes, or fats. By using air suspensions to coat medical devices, the methods of the present invention result in coatings having minimal defects and uniform thicknesses and mechanical properties. Further, the methods of the present invention are time efficient and cost effective because they facilitate the coating of numerous medical devices in a single batch, resulting in numerous medical device units containing substantially the same coating.

44 Claims, 3 Drawing Sheets

U.S. PATENT DOCUMENTS

| | | | |
|---|---|---|---|
| 4,994,013 A | * | 2/1991 | Suthanthiran et al. .......... 600/8 |
| 5,017,401 A | | 5/1991 | Van Druner |
| 5,192,308 A | | 3/1993 | Ostapchenko ................... 623/1 |
| 5,221,698 A | | 6/1993 | Amidon et al. ............. 523/122 |
| 5,236,503 A | * | 8/1993 | Jones .......................... 118/303 |
| 5,328,720 A | * | 7/1994 | Emken et al. ............... 427/213 |
| 5,405,309 A | * | 4/1995 | Carden, Jr. .................... 600/3 |
| 5,447,966 A | | 9/1995 | Hermes et al. .............. 523/113 |
| 5,464,650 A | | 11/1995 | Berg et al. .................... 427/2.3 |
| 5,611,151 A | | 3/1997 | Jacob .......................... 34/395 |
| 5,624,411 A | | 4/1997 | Tuch .......................... 604/265 |
| 5,679,400 A | | 10/1997 | Tuch .......................... 427/2.14 |
| 5,679,402 A | | 10/1997 | Lee ............................. 427/127 |
| 5,837,008 A | | 11/1998 | Berg et al. ...................... 623/1 |
| 5,837,284 A | | 11/1998 | Mehta et al. ................ 424/459 |
| 5,855,915 A | | 1/1999 | Pinkus ........................ 424/486 |
| 5,876,750 A | | 3/1999 | Jao et al. .................... 424/457 |
| 5,972,985 A | | 10/1999 | Thomas et al. ............. 514/400 |
| 5,980,882 A | | 11/1999 | Eichman .................. 428/78.12 |
| 6,046,277 A | | 4/2000 | Kolter et al. ................ 525/205 |
| 6,143,431 A | * | 11/2000 | Webster ...................... 428/669 |
| 6,174,329 B1 | | 1/2001 | Callol et al. ............... 623/1.34 |

* cited by examiner

COATING MEDICAL DEVICES USING AIR SUSPENSION

This application is a continuation-in-part of pending application Ser. No. 09/293,994 filed Apr. 19, 1999 now abandoned.

FIELD OF THE INVENTION

The present invention relates to coated medical devices, and more particularly to medical devices that are coated using air suspension.

BACKGROUND OF THE INVENTION

It is often beneficial to coat medical devices so that the surfaces of such devices have desired properties or effects. For example, it is useful to coat medical devices to provide for the localized delivery of therapeutic agents to target locations within the body, such as to treat localized disease (e.g., heart disease) or occluded body lumens. Such localized drug delivery avoids the problems of systemic drug administration, which may be accompanied by unwanted effects on parts of the body which are not to be treated, or because treatment of the afflicted part of the body requires a high concentration of therapeutic agent that may not be achievable by systemic administration. Localized drug delivery is achieved, for example, by coating balloon catheters, stents and the like with the therapeutic agent to be locally delivered. The coating on medical devices may provide for controlled release, which includes long-term or sustained release, of a bioactive material.

Aside from facilitating localized drug delivery, medical devices are coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

Conventionally, coatings have been applied to medical devices by processes such as dipping, spraying, vapor deposition, plasma polymerization, and electrodeposition. Although these processes have been used to produce satisfactory coatings, there are numerous potential drawbacks associated therewith. For example, it is often difficult to achieve coatings of uniform thicknesses, both on individual parts and on batches of parts. Also, many of these conventional coating processes require that the coated part be held during coating, resulting in defects such as bare spots where the part was held and thus requiring subsequent coating steps. Further, many conventional processes require multiple coating steps or stages for the application of a second coating material, or to allow for drying between coating steps or after the final coating step.

There is, therefore, a need for a cost-effective method of coating medical devices that results in uniform, defect-free coatings and uniform drug doses per unit device. The method would allow for a multiple stage coating in order to apply a bioactive material that may be environmentally sensitive, e.g., due to heat and light (including ultra-violet) exposure and due to degradation of the bioactive material due to process-related forces (e.g., shear). The method would thus allow for better control of the sensitivity of the bioactive material and reduce any potential degradation due to environmental issues. The method would also reduce variations in the coating properties.

SUMMARY OF THE INVENTION

In one aspect, the present invention relates to methods for coating at least a portion of a medical device which is used, at least in part, to penetrate the body of a patient. In one embodiment, the method comprises the steps of suspending the medical device in an air stream that is substantially devoid of suspending particles and introducing a coating material into the air stream such that the coating material is dispersed therein and coats at least a portion of the medical device. This process is used to apply one or more coating materials, simultaneously or in sequence. In certain embodiments of the invention, the coating materials include therapeutic agents, polymeric materials, and sugars, waxes, and fats. A coating substance that is comprised of suspension particles may be utilized that are fused to the surface of the medical device by a coating solution.

In another embodiment of the present invention, the medical devices are suspended in an air stream substantially devoid of suspending particles and a coating apparatus coats at least a portion of the medical device with a coating material while the medical devices are suspended in the air stream. The coating apparatus may include a device that utilizes any number of alternative coating techniques for coating the medical devices.

In another aspect, the present invention relates to coated medical devices made by the method of the invention.

One advantage of the present invention is that it provides coated medical devices with uniform coating thicknesses and mechanical properties and minimal contaminants.

Another advantage of the present invention is that it allows simultaneous coating of multiple numbers of medical devices at the same time, thus leading to higher process efficiency.

Another advantage of the present invention is that it does not require that the medical device be held during the coating process, thereby eliminating bare spots and the need for subsequent coating steps to coat such bare spots.

Another advantage of the present invention is that it provides a method for coating medical devices by coating materials that are otherwise difficult to use, such as incompatible, insoluble/suspension, or unstable coating solutions.

Another advantage of the present invention is that it reduces human exposure to materials used in conventional coating processes such as solvents, polymers, drugs, and the like.

Another advantage of the present invention is that it allows for the application of multiple coating materials to numerous medical devices in a single batch coating process.

Yet another advantage of the present invention is that it provides a method for coating a medical device that results in a uniform drug dose per unit device.

DETAILED DESCRIPTION

Figure 1:
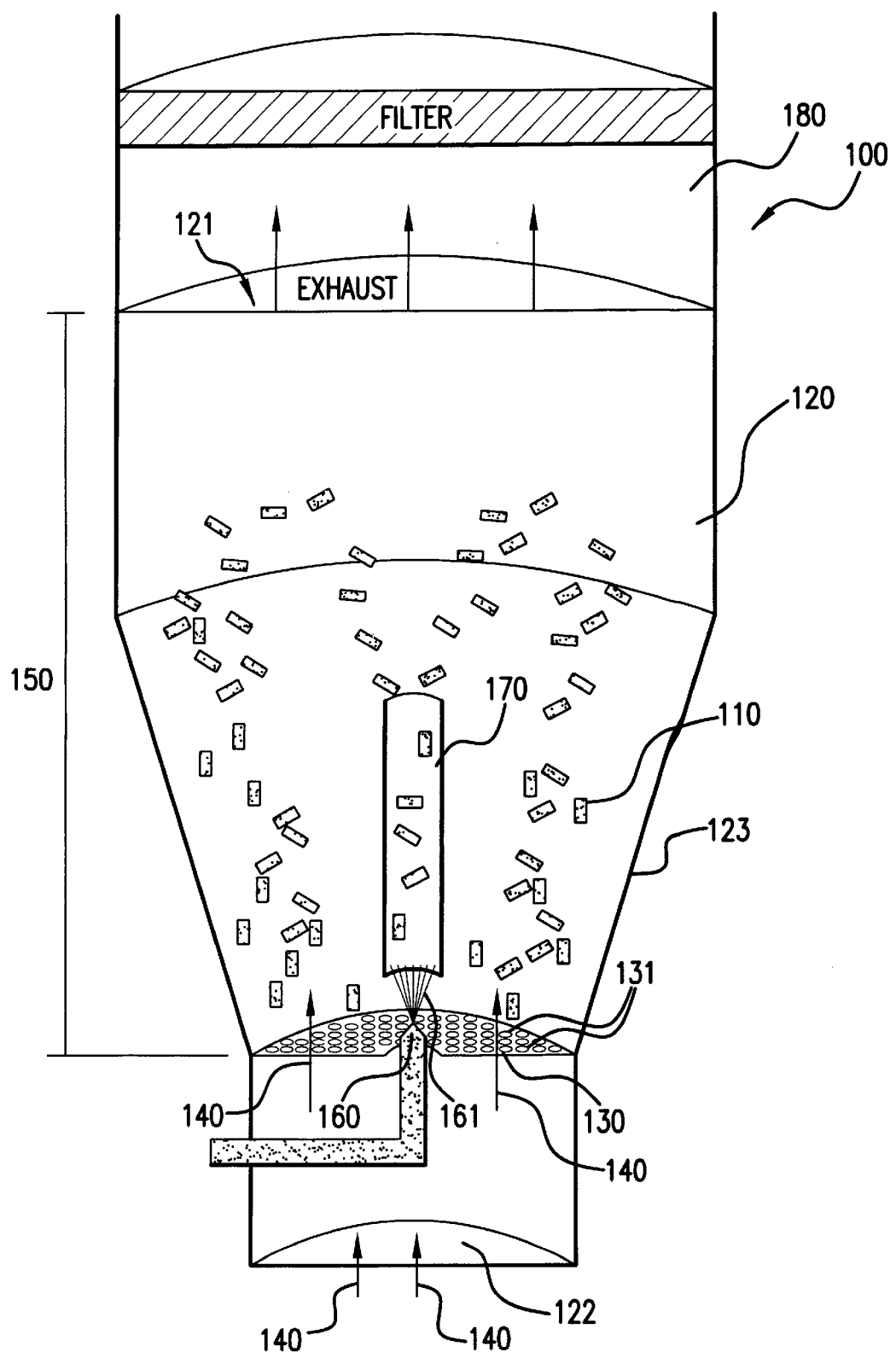
FIG. 1 is a cross-sectional view of an apparatus for coating medical devices in accordance with a first embodiment of the present invention.

The present invention provides methods for coating medical devices, and devices thereby produced. By using air suspension to coat medical devices, the methods of the present invention result in coatings having minimal defects and uniform thicknesses and mechanical properties. Further, the methods of the present invention are time efficient and cost effective because they facilitate the uniform coating of numerous medical devices in a single batch.

Whereas the present invention allows multiple medical devices to be coated as a batch, the present invention is not limited to only coating medical devices in batches, i.e., coating a group of devices in one batch process followed by coating a second group of devices in a second batch process. The methods and apparatuses of the present invention can be utilize to continuously run medical devices through the apparatuses such that the process does not have to be started and stopped for coating the medical devices in batches. The medical devices can be run through a continuous process.

In all embodiments of the present invention, single or multiple coating materials are applied to medical devices by suspending the medical devices in an air stream and coating at least a portion of the medical device. As used herein, "air stream" refers to a stream of any suitable gas, such as air, nitrogen, argon and combinations thereof. The air stream is said to be "substantially devoid of suspending particles", i.e., particles are not utilized to suspend the medical devices within the air stream. The air stream itself suspends the medical devices. Any non-coating particles (i.e., particles that do not become at least partially part of the coating materials) that may be present in the air stream do not materially provide for suspending the medical devices. Particles might be added to the air stream to enhance the coating process, e.g., a polishing media and/or electrostatic inhibitors in low ratios, however, these added particles are not used to suspend the articles to be coated. Thus, the air stream, since it is substantially devoid of suspending particles and only requires the air itself in the air stream to suspend the medical devices, may be termed a homogenous suspending air stream. As used herein, "suspending" the medical device shall refer to a-process whereby the medical device is situated within the flow of an air stream and may be moving within the air stream while unsupported by any external means.

The medical devices used in conjunction with the present invention include any device amenable to the coating processes described herein. The medical device, or portion of the medical device, to be coated or surface modified may be made of metal, polymers, ceramics, composites or combinations thereof, and for example, may be coated with one or more of these materials. Whereas the present invention is described herein with specific reference to a vascular stent, other medical devices within the scope of the present invention include any devices which are used, at least in part, to penetrate the body of a patient. Examples include implantable devices such as catheters, needle injection catheters, blood clot filters, vascular grafts, stent grafts, biliary stents, colonic stents, bronchial/pulmonary stents, esophageal stents, ureteral stents, aneurysm filling coils and other coiled coil devices, trans myocardial revascularization ("TMR") devices, percutaneous myocardial revascularization ("PMR") devices etc., as are known in the art, as well as devices such as hypodermic needles, soft tissue clips, holding devices, and other types of medically useful needles and closures. Any exposed surface of these medical devices may be coated with the methods and apparatuses of the present invention including, for example, the inside exposed surface and the outside exposed surface of a tubular medical device which is open at both ends.

The coating materials used in conjunction with the present invention are any desired, suitable substances. In some embodiments, the coating materials comprise therapeutic agents, applied to the medical devices alone or in combination with solvents in which the therapeutic agents are at least partially soluble or dispersible or emulsified, and/or in combination with polymeric materials as solutions, dispersions, suspensions, latices, etc. The terms "therapeutic agents" and "drugs" are used interchangeably herein and include pharmaceutically active compounds, nucleic acids with and without carrier vectors such as lipids, compacting agents (such as histones), virus, polymers, proteins, and the like, with or without targeting sequences. The coating on the medical devices may provide for controlled release, which includes long-term or sustained release, of a bioactive material.

Specific examples of therapeutic or bioactive agents used in conjunction with the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflanmatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such astriclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promotors; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifinctional molecules consisting of a growth factor and a cytotoxin, biflnctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagnonist, and 5-HT uptake inhibitors; cholesterol-lowering agents; vasodilating agents; agents which interfere with endogeneus vasoactive mechanisms; survival genes which protect against cell death, such as anti-apoptotic Bcl-2 family factors and Akt kinase; and combinations thereof; and beta blockers. These and other compounds may be added to a coating solution, including a coating solution that includes a polymer, using similar methods and routinely tested as set forth in the specification. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be incorporated into the polymer coating, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing anupstream or downstream effect of a BMP can be provided. Such molecules include any of the "hedgehog" proteins, or the DNA's encoding them.

Coating materials other than therapeutic agents include, for example, polymeric materials, sugars, waxes, and fats, applied alone or in combination with therapeutic agents, and monomers that are cross-linked or polymerized. Such coating materials are applied in the form of, for example, powders, solutions, dispersions, suspensions, and/or emulsions of one or more polymers, optionally in aqueous and/or organic solvents and combinations thereof or optionally as liquid melts including no solvents. When used with therapeutic agents, the polymeric materials are optionally applied simultaneously with, or in sequence to (either before or after), the therapeutic agents. Such polymeric materials employed as, for example, primer layers for enhancing subsequent coating applications (e.g., application of alkanethiols or sulfhydryl-group containing coating solutions to gold-plated devices to enhance adhesion of subsequent layers), layers to control the release of therapeutic agents (e.g., barrier diffusion polymers to sustain the release of therapeutic agents, such as hydrophobic polymers; thermal responsive polymers; pH-responsive polymers such as cellulose acetate phthalate or acrylate-based polymers, hydroxypropyl methylcellulose phthalate, and polyvinyl acetate phthalate), protective layers for underlying drug layers (e.g., impermeable sealant polymers such as ethylcellulose), biodegradable layers, biocompatible layers (e.g., layers comprising albumin or heparin as blood compatible biopolymers, with or without other hydrophilic biocompatible materials of synthetic or natural origin such as dextrans, cyclodextrins, polyethylene oxide, and polyvinyl pyrrolidone), layers to facilitate device delivery (e.g., hydrophilic polymers, such as polyvinyl pyrrolidone, polyvinyl alcohol, polyalkylene gylcol (i.e., for example, polyethylene glycol), or acrylate-based polymer/copolymer compositions to provide lubricious hydrophilic surfaces), drug matrix layers (i.e., layers that adhere to the medical device and have therapeutic agent incorporated therein or thereon for subsequent release into the body), and epoxies.

When used as a drug matrix layer for localized drug delivery, the polymer coatings of the present invention comprise any material capable of absorbing, adsorbing, entrapping, or otherwise holding the therapeutic agent to be delivered. The material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyurea, polyacrylate, polyacrylic acid and copolymers, polyorthoesters, polyanhydrides such as maleic anhydride, polycarbonates, polyethylene, polypropylenes, polylatic acids, polystyrene, natural and synthetic rubbers and elastomers such as polyisobutylene, polyisoprene, polybutadiene, including elastomeric copolymers, such as Kraton®, styrene-isobutylene-styrene (SIBS) copolymers; polyglycolic acids, polycaprolactones, polyhydroxybutyrate valerates, polyacrylamides, polyethers, polysaccharides such as cellulose, starch, dextran and alginates; polypeptides and proteins including gelatin, collagen, albumin, fibrin; copolymers of vinyl monomers such as ethylene vinyl acetate (EVA), polyvinyl ethers, polyvinyl aromatics; other materials such as cyclodextrins, hyaluronic acid and phosphorylcholines; and mixtures and copolymers thereof. Coatings from polymer dispersions such as polyurethane dispersions (BAYHDROL, etc.) and acrylic latex dispersions are also within the scope of the present invention. Preferred polymers include polyurethanes; polyacrylic acid as described in U.S. Pat. No. 5,091,205, the disclosure of which is incorporated herein by reference; and aqueous coating compositions comprising an aqueous dispersion or emulsion of a polymer having organic acid functional groups and a polyfunctional crosslinking agent having functional groups capable of reacting with organic acid groups, as described in U.S. Pat. No. 5,702,754, the disclosure of which is incorporated herein by reference.

The release rate of drugs from drug matrix layers is largely controlled, for example, by variations in the polymer structure and formulation, the difflusion coefficient of the matrix, the solvent composition, the ratio of drug to polymer, potential chemical reactions and interactions between drug and polymer, the thickness of the drug adhesion layers and any barrier layers, and the process parameters, e.g., drying, etc. The coating(s) applied by the methods and apparatuses of the present invention may allow for a controlled release rate of a coating substance with the controlled release rate including both long-term and/or sustained release.

Additionally, a coating substance may include suspension particles, e.g., a powder. The suspension particles are not utilized for suspending the medical devices, but rather, are coated onto the medical devices. For example, the suspension particles may be fused to the surface of the medical device by a coating solution.

The coatings of the present invention are applied such that they result in a suitable thickness, depending on the coating material and the purpose for which the coating(s) is applied. As an example, coatings applied for localized drug delivery are typically applied to a thickness of about 1 to 30 microns, preferably about 2 to 20 microns. Very thin coatings, e.g., of about 100 Å, and much thicker coatings, e.g., more than 30 microns, are also possible. It is also within the scope of the present invention to apply multiple layers of the same or different coating materials, which may perform identical or different functions (e.g., to provide for biocompatibility, to control drug release, etc.). In accordance with a first embodiment of the present invention, medical devices are coated by suspending the medical device in an air stream substantially devoid of suspending particles having a first coating material dispersed therein, by any corresponding, suitable method. For illustrative purposes only, the first embodiment of the invention is described with specific reference to the so-called "Wurster process" shown in FIG. 1. The Wurster process is described in U.S. Pat. No. 3,253,944, which is incorporated herein by reference. Such a process has been proposed for use to coat pharmaceutical tablets with waxes (see, e.g., D. M. Jones, "Factors to Consider in Fluid-Bed Processing," 9 *Pharm. Tech.* 50–62 (1985), and A. M. Mehta, "Scale-Up Considerations in the Fluid-Bed Process for Controlled-Release Products," 12 *Pharm. Tech.* (1988)), but has not been proposed or used to coat medical devices.

As stated above, the first embodiment for an apparatus for coating medical devices 100 in accordance with the principles of the present invention is illustrated in FIG. 1. In FIG. 1, medical devices 110 are placed in a chamber 120. The chamber 120 includes a top opening 121 for exhaust, a bottom opening 122 for introduction of input air 140, and at least one side wall 123. Although the chamber 120 is shown to generally include a structure having a tapered, cylindrical shape, the chamber 120 may be of any suitable shape, such as rectangular. The tapered configuration of the chamber 120 as shown in FIG. 1 is generally preferred to facilitate a cyclical air flow within the chamber 120. The coating process of the present invention occurs within the chamber 120.

The embodiment 100 includes an air distribution plate 130, which is secured to the side wall 123 of the chamber 120. The air distribution plate 130 has openings 131 that are smaller than the smallest dimension of the medical devices 110 so that the medical devices 110 cannot fall through it. The purpose of the air distribution plate 130 is to channel input air 140, introduced into the chamber 120 from its bottom opening 122, into the coating region 150 of the chamber 120 to assist in the fluidization and coating of the medical devices 110. The air distribution plate 130 is of any suitable shape to achieve this purpose, such as planar (as shown in FIG. 1) or concave configurations.

The air distribution plate 130 is of any suitable structure that permits the flow of air therethrough such as, for example, a perforated metal or ceramic plate or screen. Preferably, the air distribution plate 130 has an open area (i.e., the planar surface area of openings) of about 4 to about 30 percent, such as about 4, 6, 8, 12, 16 or 30 percent. A specific example of the air distribution plate 130 is a stainless steel screen having an opening size of about 60 to about 325 mesh. The open area and opening size of the air distribution plate 130 are selected to provide for the optimum suspension and coating of the medical devices 110 within the coating region 150. For example, an air distribution plate 130 having a large open area will result in a relatively low velocity of air within the coating region 150, and is thus used for low density medical devices 110. Conversely, an air distribution plate 130 having a small open area will result in a relatively high velocity of air within the coating region 150, and is thus used for high density medical devices 110. The air distribution plate can be either fixed or rotating to facilitate more even distribution of air.

The embodiment 100 further includes a nozzle 160 extending through the air distribution plate 130 and into the coating region 150. The nozzle injects an air stream 161, which in this embodiment includes a coating material dispersed therein, into the coating region 150. As shown in FIG. 1, the nozzle 160 is preferably located at or near the longitudinal axis of the chamber 120. The embodiment 100 optionally includes multiple nozzles situated at various locations within the chamber 120, such as along the side 123, top, or bottom of the chamber 120. In this embodiment, the nozzle 160 is used to introduce one or more coating materials, sequentially or simultaneously, into the chamber 120. Where multiple coating materials are introduced into chamber 120, they may be either mixed and introduced at nozzle 160, i.e., in-line mixed, or may be introduced into chamber 120 though nozzle 160 and/or from the nozzles located at the top or bottom of the chamber.

Both air streams 161 and 140 are substantially devoid of suspending particles, as discussed above, and the air streams may consist of one or more gases. Because the air streams are substantially devoid of any suspending particles, the surface areas of the medical devices to be coated when in the air stream(s) are not subject to being obscured by, and/or damaged by contact with, the suspending particles, which could deleteriously impact the coating of the surface areas of the medical devices. In an embodiment, air stream 161 is characterized by a higher velocity than air stream 140 that is channeled through the air distribution plate 130 to cause a cyclical air flow and corresponding medical device movement within the coating region 150. In other words, the high-velocity air stream 161 causes the medical devices 110 to be lifted from or near the air distribution plate 130 towards the top opening 121 of the chamber 120. When the air stream 161 can no longer support the medical devices 110, they fall through the lower-velocity air stream 140 along the sides of the chamber 120. The velocity of the air stream 140 is sufficient to slow, but not to stop or reverse, the fall of the medical devices 110. When the medical devices 110 approach or fall on the air distribution plate 130, they are again lifted by the high-velocity air flow 161. Thus, air streams 161 and 140 are of a sufficient velocity such that the air streams themselves are able to suspend the medical devices within the coating region. Thus, no suspending particles are required in the air streams to suspend the medical devices to be coated.

In an embodiment where multiple nozzles are used, nozzle 160, centrally located near the air distribution plate 130 as shown in FIG. 1, may be the only nozzle associated with a high-velocity air stream. Any other nozzles may be only used to inject the coating material(s) into the chamber 120 at a low velocity so as not to disrupt the cyclical flow of air and medical devices.

An optional partition 170, which is preferably tubular in shape, may be attached to the side wall 123 of the chamber 120 and extend along the longitudinal axis of the chamber 120 to help facilitate the cyclical air flow within the chamber 120 and to ensure the separation of rising and falling medical devices 110, thus minimizing potentially damaging interactions. Also optional is a gas exhaust duct 180, which is preferably associated with top opening 121 and which may include a filter.

In an alternative embodiment, the air streams 161 and 140 may be of substantially equal velocity. In this embodiment, the flow/velocity of the two air streams at the center of the chamber 120 would be additive to effectively create a greater flow/velocity of air at the center of the chamber in comparison to the flow/velocity of the air at the sides of the chamber, thus providing for cyclical movement of the medical devices as described above.

In yet another alternative embodiment, only one of air streams 161 or 140 are utilized. For example, the airstream 161 is utilized to both suspend the medical devices and introduce the coating material(s) into chamber 120. A cyclical flow of air within the chamber could be provided by varying the velocity of the one air stream across it's flow pattern, such as, for example, by appropriately configuring the openings in air distribution plate 130.

Although the embodiment 100 making use of the Wurster process is generally preferred for making the coated medical devices of the present invention, any suitable method or apparatus can be used. For example, medical devices may be loaded into a conventional fluidized bed chamber, in which air is introduced into a "bed" or layer of the medical devices from below while the coating material is sprayed onto the fluidized devices from above. In such a process, the medical devices will move randomly within a fluidized bed. Airless and atomized air spray processes are also within the scope of the present invention. Although not required by the present invention, coating within a closed chamber is generally preferred because of the corresponding ability to control the coating processing parameters and the chamber environment. For example, it is advantageous to control processing parameters such as the fluidization air composition, temperature and humidity when coating with drugs or polymers that degrade, oxidize, hydrolyze, etc., upon exposure to specific environments. The present invention may be utilized to coat medical devices with organic-based coating materials. Thus, operating temperatures in at least some embodiments of the apparatuses and methods of the present invention are generally less than 500° C., with some embodiments having an operating temperature of between 0° C.–200° C. The particular operating temperatures utilized are compatible with the particular coating materials. Thus, operating temperatures compatible with all of the coatings materials disclosed herein can be established and maintained in the apparatuses and methods of the present invention.

In other alternative embodiments of the present invention, instead of applying a coating as a preformed substance, the material of the coating would be generated in the spraying process. The suspended medical devices to be coated could be sprayed first with a polyfunctional condensation monomer followed by spraying with a complementary condensation polyfinctional monomer to provide a polymer coating by interfacial polymerization. For example, a glycol or diamine could be sprayed on first followed by a diisocyanate to form a polyurethane or polyurea. A potential advantage of this process would be to avoid the need for volatile solvents, application of lower viscosity fluids to improve coverage, and to provide crosslinked polymer coating that would be impossible to obtain by conventional coating techniques, e.g., by use of trifunctional monomers.

Other alternative embodiments for coating of the medical devices include apparatuses and methods that do not involve dispensing the coating material using an air stream through, for example, nozzle 160 as discussed above in connection with FIG. 1. These alternative apparatuses and methods for coating the medical devices still utilize an air stream and the structure of FIG. 1, as described above, to suspend the medical devices in a coating chamber; however, the medical devices could be coated by using alternative coating techniques. These alternative coating techniques could also be utilized with the fluidized bed chamber contemplated above.

Figure 2:
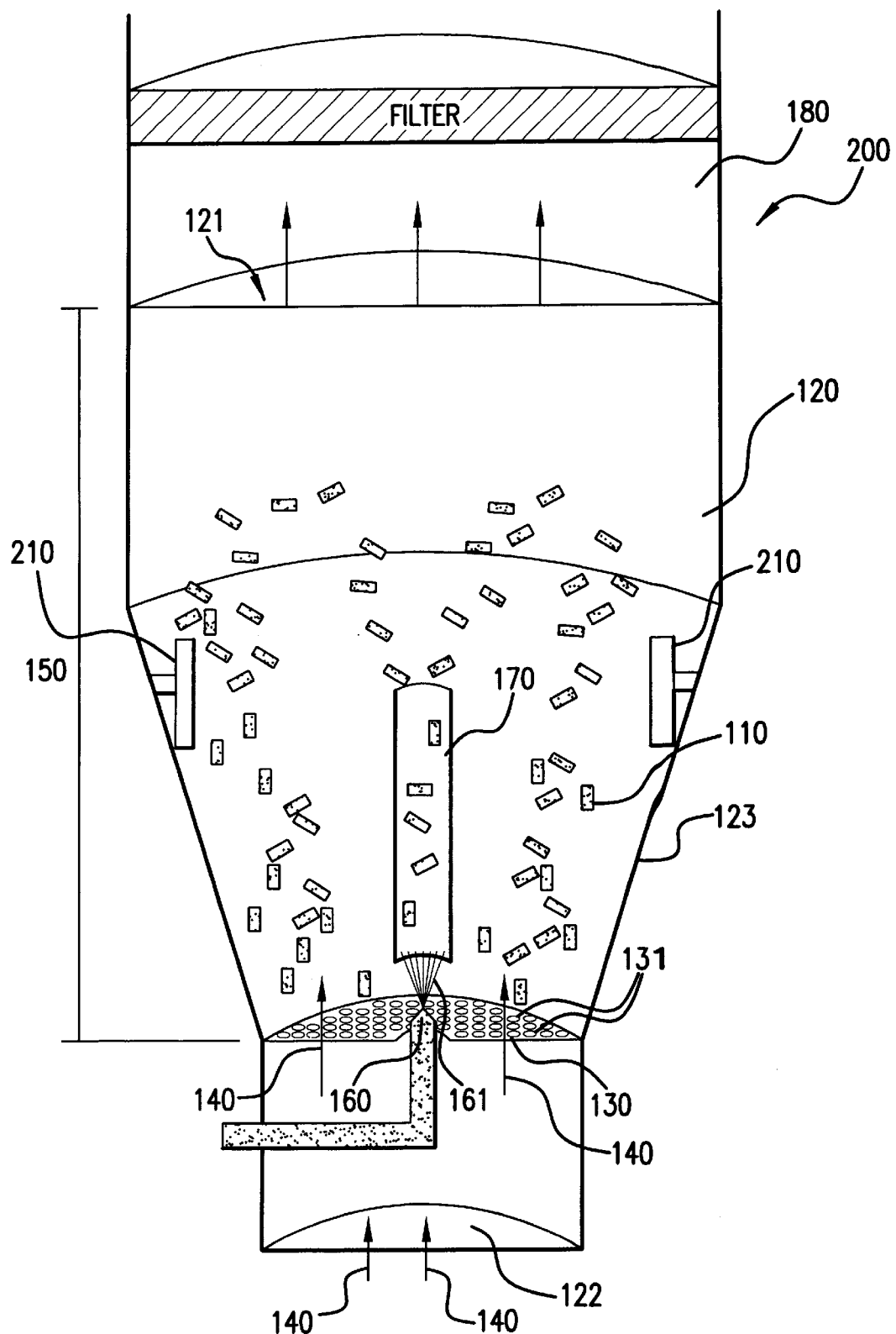
FIG. 2 is a cross-sectional view of an apparatus for coating medical devices in accordance with a second embodiment of the present invention.

Thus, a second embodiment for an apparatus for coating medical devices 200 in accordance with the principles of the present invention is illustrated in FIG. 2. The embodiment of FIG. 2 utilizes a structure similar to that described for the embodiment of FIG. 1, however, in the embodiment of FIG. 2, the coating material may not be dispersed within air stream 161 by nozzle 160. In the embodiment of FIG. 2, both or one of the air streams 161 and 140 are utilized to suspend the medical devices within chamber 120. A coating apparatus 210 is utilized to apply the coating to the suspended medical devices. Depending upon the particular coating apparatus used, a coating material may be introduced into the coating chamber by the coating apparatus itself, by one or both of air streams 161 and 140, or through any other well-known means that are associated with the particular coating apparatus utilized. For reference purposes, the components for embodiment 200 in FIG. 2 that are common to those of embodiment 100 of FIG. 1 are designated by like reference numerals.

In the embodiment of FIG. 2, the coating apparatus 210 may include a device(s) that permit the use of any number of alternative techniques for coating the medical devices. As discussed previously, the coating apparatus may apply a single coating or multiple coatings to the medical device. Additionally, the coating apparatus may apply coatings to any of the different types of medical devices disclosed previously in this specification. The apparatus may also apply any of a variety of coating materials as described previously.

The coating apparatus 210 may be utilized to apply one or more coatings to medical devices by utilizing any of the following exemplary techniques and the associated devices for these techniques for application of the coatings.

Ionization deposition processes can be utilized to apply coatings to medical devices. Ionization deposition processes such as ion beam-assisted deposition (IBAD), ion beam (IB), and ion beam implantation (IBI). Examples of materials that can be deposited/implanted include nitrogen, gold, silver, tungsten, titanium, aluminum, silicon, iron, nickel, selenium, tantalum, diamond-like carbon (DLC), ceramics, radioactive materials such as palladium-103, $^{60}$Co, $^{192}$Ir, $^{32}$P, $^{111}$In, $^{90}$Y, and $^{99}$Tc.

Plasma treatment, grafting, or deposition processes can be used to coat or modify the surface of the medical device or a part of the medical device with the following materials: monomers or oligomers, cyclic and acrylic siloxanes, silanes, silylimidazoles, fluorine-based monomers (hydrofluorocarbons), aliphatic and aromatic hydrocarbons, acrylic monomers, N-vinyl pyrrolidone, vinyl acetate, ethylene oxide, one or more monomers used alone or in combination in order to form blends, cross-linked polymers, copolymers and interpenetrating network polymers. Plasma treatment may also be used to enhance crosslinking and/or improve surface properties such as adhesion, lubricity, or conductivity.

Figure 3:
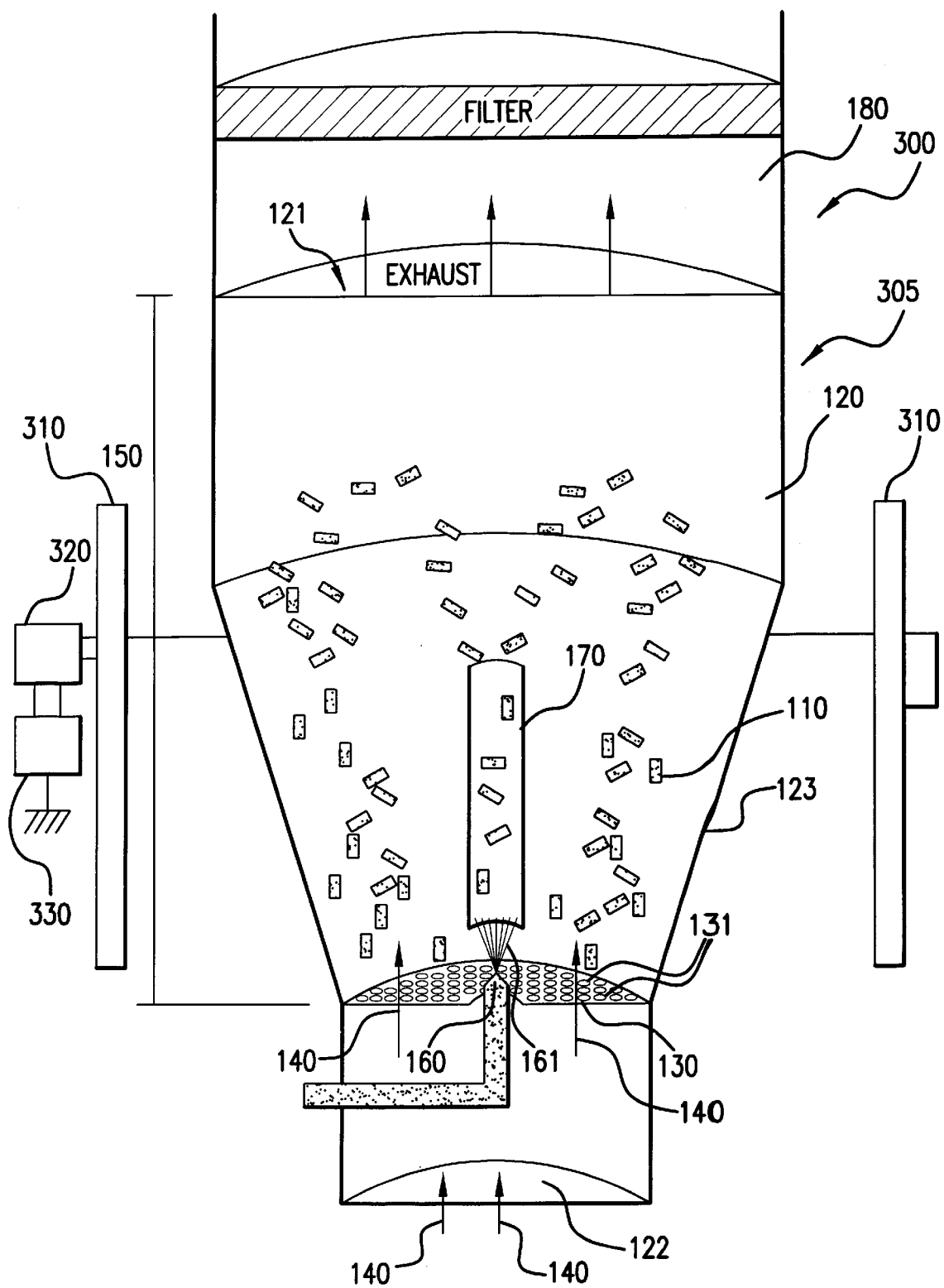
FIG. 3 illustrates a plasma coating apparatus in accordance with the principles of the present invention.

FIG. 3 illustrates a particular alternative embodiment for an apparatus for coating medical devices 300 in accordance with the principles of the present invention where the coating apparatus 210 of FIG. 2 is a plasma coater 305. As described in connection with FIG. 2, in the embodiment of FIG. 3, both or one of the air streams 161 and 140 are utilized to suspend the medical devices within chamber 120; however, a plasma coater 305 is utilized to coat the suspended medical devices. For reference purposes, the components for embodiment 300 in FIG. 3 that are common to those of embodiments 100 and 200 of FIGS. 1 and 2, respectively, are designated by like reference numerals. Plasma coater 305 includes electrodes 310, a matching network 320, and a RF (radio frequency) generator 330. The materials to be coated on the medical devices may be introduced-into chamber 120 through either of air streams 161 and/or 140 or through any other means, such as by depositing the coating material on air distribution plate 130 and having the air stream(s) dispense the coating material into the chamber. The coating material(s) are then applied to the medical devices by using plasma coater 305.

In continuing with the discussion of the alternative coating techniques that may be utilized in the present invention, chemical vapor deposition processes are also within the scope of the present invention. Processes such as polyamide, polyimide, parylene, and parylene derivatives, polyalkylene oxide, polyalkylene glycol, polypropylene oxide, silicone based polymers, polymers of methane, tetrafluoroethylene or tetramethyldisiloxane or polymers from photopolymerizable monomers or combinations thereof.

Electroplating and electrostatic deposition processes may be utilized in the present invention as well as deposition, polymerization or treatment of part of the medical device surface or the entire device surface using microwave, ultraviolet light (UV), visible lingt, electron-beam, and thermal evaporation techniques.

In any embodiment of the present invention, the apparatuses and methods of the present invention result in the complete or partial coating of the medical device to be coated. Partial coating is accomplished, for example, using known masking or similar techniques to result in the coating of predetermined struts or stent segments. The various coating techniques may be used in conjunction with one another and, thus, they are not mutually exclusive.

In addition to the previously described coating layers and their purposes, in the present invention the coating layer or layers may be applied for any of the following additional purposes or combination of the following purposes:

Alter surface properties such as lubricity, contact angle, hardness, or barrier properties.

Improve corrosion, humidity and/or moisture resistance.

Improve fatigue, mechanical shock, vibration, and thermal cycling.

Change/control composition at surface and/or produce compositionally graded coatings.

Apply controlled crystalline coatings.

Apply conformal pinhole free coatings.

Minimize contamination.

Change radiopacity.

Impact bio-interactions such as tissue/blood/fluid/cell compatibility, antiorganism interactions (fungus, microbial, parasitic microorganisms), immune response (masking).

Control release of incorporated therapeutic agents (agents in the base material, subsequent layers or agents applied using the above techniques or combinations thereof).

Or combinations of the above using single or multiple layers.

In addition to the benefits of the apparatus and methods of the present invention that have been discussed previously in this specification and in further amplification of some of the benefits discussed previously, the present invention can provide the following advantages.

Coating in an air stream allows many medical devices or parts of medical devices to be coated simultaneously in batch process, which eliminates variability that could arise if each object is coated and handled individually.

Part to part variability is minimized because all the objects are coated under identical conditions at the same time.

Uniformity of the coated layer, layers, or surface modification is achieved over the entire surface of interest using careful control and optimization of the coating parameters.

In situations where the device, part of the device and/or any subsequently coated layers contain one or more therapeutic agents, the methods yield a uniform, well-defined rate controlling membrane, or a uniformly coated layer incorporating the therapeutic agents. This results in uniform controlled drug release for devices, parts of devices, and/or coatings that contain active components.

Drug reconciliation and traceability (a critical issue in finished pharmaceutical manufacturing processes) is maximized using this type of contained manufacturing process in situations where the device, part of the device, and/or any subsequently coated layers contain one or more therapeutic agents.

No defects will form on the surface as a result of holding the device during coating since the coating is applied to the device while the device is levitated in the air stream.

Worker exposure to harmful chemicals, or components is minimized because the process proceeds under sealed conditions.

One coater may be used to apply more than one type of coating and/or surface modification if the equipment is designed to handle combinations of several coating techniqued such as air atomization, ionization deposition, plasma, chemical vapor deposition, electroplating, electrostatic, UV, microwave, visible, and electron-beam.

The invention is further described with reference to the following non-limiting examples.

EXAMPLE 1

Coronary stents are coated with a polymeric coating solution in accordance with the present invention.

Numerous (approximately 300 to 600 in this example) NIR stents (Medinol, Tel Aviv) are placed in a Wurster fluidized bed chamber, such as a GPCG-1 (available from Glatt Air Techniques, Ramesey, N.J.). The stents are each about 9 mm–32 mm in length, about 1.5 mm–3.0 mm in diameter, about 7 mg–35 mg in weight, and about 46–200 mm$^2$ in surface area.

A coating solution of polyurethane is prepared by mixing the following components (in approximate weight percentages): 0.5–1.0% Corethane 50D (Corvita, Miami, Fla.), 1.0–10.0% dimethylacetamide, and balance tetrahydrofuran. The solution components are mixed using a magnetic stirrer for at least about 8 hours to form a solution or dispersion, which is thereafter filtered with a 1.0 micron Teflon filter.

The stents are suspended using fluidizing air at about 2–20 psi, at a temperature of about 20–90° C. and a dew point of about 10–60° C. The stents are coated by pumping about 100–400 gm of the coating solution at about 0.1–6 ml/min to a nozzle located at the center of the perforated plate. The coating solution is atomized with compressed atomizing air operating at a pressure of about 2–40 psi and a flow rate of about 5 cfm. The atomizing air has a temperature of about 10–60° C. and a dew point of about 0–40° C.

Coating of the suspended stents continues until all of the coating solution has been pumped through the nozzle. Following the coating process, the stents are continued to be suspended for about 5–180 minutes to allow for the polymer coating layer to completely dry. After drying, the stents are removed from the Wurster fluidization chamber.

Because the stents are suspended in an air stream during the coating process, the coated stents do not display surface defects that normally result when a stent is held during coating. In addition, this is a batch process in which each stent is exposed to identical process conditions. The coating thickness depends on the size of the stent and the amount of the coating solution applied. As a result of the good control over processing parameters during coating, the coating on each stent strut is substantially identical.

EXAMPLE 2

Coronary stents are coated with a layer that comprises both polymeric and drug coating materials in accordance with the present invention.

NIR stents are placed in a Wurster fluidized bed chamber, as described in Example 1. A coating solution is prepared by mixing the following components (in approximate weight percentages): about 0.5–2.0% Elvax 40W (available from Dupont, Wilmington, Del.), about 0.05–0.6% paclitaxel, balance chloroform. The coating solution components are mixed with a magnetic stirrer for at least 8 hours to form a solution or dispersion, which is thereafter filtered with a 0.2 micron Teflon filter.

The stents are suspended and coated by the processing parameters described in Example 1. The coating process results in stents coated with uniform coating layers in which paclitaxel is evenly distributed on each stent and substantially the same dose applied to every stent in the batch.

EXAMPLE 3

Coronary stents are coated with multiple polymer coating layers in sequence distributed on each stent and the same dose applied to every stent in the batch in accordance with the present invention.

NIR stents are placed in a Wurster fluidized bed chamber, as described in Example 1. A primer coating solution is prepared by mixing the following components (in approximate weight percentages): 0.01–2% Ultrathene UE631-04 (Equistar Chemical, LP, Houston, Tex.) and 99% Chloroform. The stents are suspended and coated by the processing parameters described in Example 1. When the primer coating is completely dry, the stents are further coated with a topcoat solution comprising (in approximate weight percentages): 0.5–0.65% Corethane 50D polyurethane, 1.0–10.0% dimethylacetamide, and balance tetrahydrofuran, prepared by the process described in Example 1.

The coating process results in stents having uniform, dual-layered coatings. The application of the primer coating enhances the adhesion of the topcoat layer to the stents. In addition, by applying several layers in sequence without removing the stents from the fluidization chamber, exposure of the stents to an outside environment between layers is minimized.

EXAMPLE 4

As a variation to Example 2, a barrier layer is applied to the stents coated with a polymer/drug layer in accordance with the present invention. A barrier layer of ethylene vinyl acetate copolymer or silicone protects the underlying polymer/drug layer from atmospheric degradation such as by oxidative or hydrolytic breakdown. The barrier layer also preferably improves abrasion resistance and durability, or may be used to control the start or rate of release of the drug from the underlying polymer/drug layer in vivo.

The barrier layer is the same or different composition as the polymer in the polymer/drug layer. For example, the barrier layer optionally comprises a dilution of MED-6605 (Nusil Silicone Technology, Carpinteria, Calif.) to 1% solids using chloroform. The hydrophobic silicone barrier reduces the release rate from the polyurethane/paclitaxel layer. Coating of both the barrier layer and polymer/drug layer is preferably conducted in sequence without removing the stents from the fluidization chamber.

The release profile of the drug may also be altered by concurrently applying several layers of gradient concentrations to yield a multi-phasic release profile. For example, the ratio of copolymers of polylactic acid ("PLA") and polyglycolic acid ("PGA") (Birmingham Polymers, Birmingham, Ala.) containing 0.1–10% of a peptide analog such as an analog of Somatostatin may be varied sequentially so that the drug has multiple peak release drug concentrations. For example, the initial coated layer may comprise PLA with drug, followed by 85:15 DL-PLG with drug, followed by 75:25 DL-PGA followed by 65:35 DL-PLG and 50:50 DL-PLG with drug, and so on. The release rate from each layer is optionally different such that the final result is several different peaks corresponding to the release from each individual layer. Layers are not limited to a single drug.

EXAMPLE 5

The invention includes the sequential application of several layers that contain components that are incompatible or do not share a common solvent system. For example, an initial coating layer applied to a medical device may contain paclitaxel and corethane polyurethane coated from solutions containing dimethylacetamide and tetrahydrofIran. A second coating layer may comprise an aqueous-based coating formulation containing agents that enhance surface biocompatibility such as heparin or albumin. For example, paclitaxel-PU is applied as a solution in dimethyl acetamide as a first layer, followed by application of heparin and/or polyethyleneglycol in aqueous solution as a second layer. As yet another example, benzalkonium chloride (a cationic surface-active agent) is applied as a first layer, followed by heparin (an anionic biocompatible polysaccharide) as a second layer, thus forming an ionic bond.

The invention includes parallel applications of drug(1)-solvent(1) and polymer(1)-solvent(2), where the drug and polymer are soluble in different solvents or are incompatible or unstable when present together. As an example, the invention is used for the simultaneous application of aqueous solution of doxorubicin hydrochloride and silicone polymer in tetrahydrofiran from two separate feeds, wherein the latter is used to form a drug-matrix in situ and to control release kinetics. As another example, DNA solution is simultaneously applied with cationic lipid systems from two separate feeds to eliminate shelf-life stability issues associated with DNA-lipid complex formulations that exhibit undesirable increases in size and turbidity as a function of salt concentration.

The invention includes parallel applications of drug(1)-polymer(1)-solvent(1) and drug(2)-polymer(2)-solvent(2) to eliminate compatibility or solubility issues- Examples include the simultaneous application of (i) cisplatin-hydroxypropyl methyl cellulose-water and paclitaxel-PCL/PLA-chloroform from two different feeds; (ii) albumin or gelatin solution from one feed and gluraldehyde crosslinker from second feed; and (iii) acrylate monomer solution from one feed and methylene bis acrylamide as crosslinker for the second feed.

The simultaneous coating of medical devices with incompatible coating materials is carried out, for example, by introducing separate feed streams into a coating chamber via separate nozzles. When compared to conventional coating techniques such as dip coating and spray coating, this embodiment of the invention substantially expands the number of coating formulations and combinations of polymers and drugs that may be coated onto medical devices. For example, an aqueous-based solution containing a desired therapeutic substance is atomized simultaneously with a solvent-based polymer coating solution.

EXAMPLE 6

The invention includes the coating of medical devices with coating materials from low-viscosity aqueous or non-aqueous solutions that would otherwise be difficult to achieve via dip-coating or spray coating applications. For example, peptide and protein drugs, which often undergo denaturation in the presence of organic solvents or excessive heat, are easily coated onto medical devices in accordance with the present invention. In such applications, the drug is applied from an aqueous formulation and the coating process is controlled (i.e., in terms of temperature and humidity) to minimize drug degradation. As another example, low viscosity solutions of RGD peptides or phosphorylcholines are deposited as monolayers or as thicker coatings for use as drug delivery depots.

The present invention provides methods of coating medical devices using air suspension, and devices thereby produced. Although the present invention has been described with respect to several exemplary embodiments, there are many other variations of the above-described embodiments which will be apparent to those skilled in the art, even where elements have not explicitly been designated as exemplary. It is understood that these modifications are within the teaching of the present invention, which is to be limited only by the claims appended hereto.

What is claimed is:

1. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes ionization deposition.

2. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes at least one of plasma treatment, plasma grafting or plasma deposition.

3. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes chemical vapor deposition.

4. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes electrostatic deposition.

5. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes at least one of a microwave deposition, microwave polymerization, or microwave treatment process.

6. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes at least one of an ultraviolet deposition, ultraviolet polymerization, or ultraviolet treatment process.

7. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes at least one of a visible light deposition, visible light polymerization, or visible light treatment process.

8. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes at least one of an electron-beam deposition, electron-beam polymerization, or electron-beam treatment process.

9. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said step of coating at least a portion of said surface of said medical device with a first coating material includes at least one of a thermal evaporation deposition, thermal evaporation polymerization, or thermal evaporation treatment process.

10. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said first coating material comprises a therapeutic agent.

11. The method of claim 10, wherein said first coating material further comprises a polymer, sugar, wax, or fat.

12. The method of claim 10, wherein said therapeutic agent is selected from the group consisting of pharmaceutically active compounds, proteins, oligonucleotides, DNA compacting agents, recombinant nucleic acids, gene/vector systems, and nucleic acids.

13. A method for coating at least a portion of a medical device for placement into a body lumen of a patient, comprising:

providing a medical device having a surface;

suspending said medical device in an air stream, said air stream substantially devoid of suspending particles; and coating at least a portion of said surface of said suspended medical device with a first coating material, wherein said first coating material comprises a polymer, sugar, wax, or fat.

14. The method of claim 13, wherein said first coating material further comprises a therapeutic agent.

15. The method of claim 13, wherein said polymer is selected from the group consisting of polycarboxylic acids, cellulosic polymers, gelatin, proteins, polypeptides, polyvinylpyrrolidone, maleic anhydride polymers, polyamides, polyvinyl alcohols, polyethylene oxides, glycosaminoglycans, polysaccharides, polyesters, polyurethanes, polystyrenes, copolymers, silicones, polyorthoesters, polyanhydrides, copolymers of vinyl monomers, polycarbonates, polyethylenes, polypropylenes, polylactic acids, polyglycolic acids, polycaprolactones, polyhydroxybutyrate valerates, polyacrylamides, polyethers, polyurethane dispersions, polyacrylates, acrylic latex dispersions, polyacrylic acid, mixtures and copolymers thereof, and monomers that are cross-linked or polymerized on said first coating material.

16. The method of claim 10, wherein said first coating material further comprises a solvent in which said therapeutic agent is at least partially soluble.

17. The method of claim 10, wherein said first coating material further comprises a solvent in which said therapeutic agent is at least partially dispersed.

18. The method of claim 13, wherein said first coating material further comprises a solvent in which said polymer, sugar, wax, or fat is at least partially soluble.

19. The method of claim 13, wherein said first coating material further comprises a solvent in which said polymer, sugar, wax, or fat is at least partially dispersed.

20. The method of claim 13, wherein said first coating material further comprises a solvent wherein said solvent is aqueous or non-aqueous.

21. A method for coating at least a portion of a medical device for placement into a body lumen of a patient, comprising:

providing a medical device having a surface;

suspending said medical device in an air stream, said air stream substantially devoid of suspending particles;

coating at least a portion of said surface of said suspended medical device with a first coating material; and coating at least a portion of said surface of said medical device with a second coating material.

22. The method of claim 21 wherein said step of coating at least a portion of said surface of said medical device with a second coating material includes the step of introducing said second coating material into said air stream such that said second coating material is dispersed therein.

23. The method of claim 21 wherein said step of coating at least a portion of said surface of said medical device with said second coating material is conducted after said step of coating a least a portion of said surface of said medical device with said first coating material is completed thereby providing an outer coating of said second coating material on said medical device.

24. The method of claim 21 wherein said step of coating at least a portion of said surface of said medical device with said second coating material is conducted simultaneously with said step of coating a least a portion of said surface of said medical device with said first coating material.

25. The method of claim 21 wherein said first coating material comprises apolymer, sugar, wax, or fat and said second coating material comprises a therapeutic agent.

26. The method of claim 25 wherein said step of coating at least a portion of said surface of said medical device with said second coating material is conducted after said step of coating a least a portion of said surface of said medical device with said first coating material is completed.

27. The method of claim 25 wherein said step of coating at least a portion of said surface of said medical device with said second coating material is conducted simultaneously with said step of coating a least a portion of said surface of said medical device with said first coating material.

28. A method for coating at least a portion of a medical device for placement into a body lumen of a patient, comprising:
providing a medical device having a surface wherein said medical device comprises a catheter;
suspending said medical device in an air stream, said air stream substantially devoid of suspending particles; and
coating at least a portion of said surface of said suspended medical device with a first coating material.

29. A method for coating at least a portion of a medical device for placement into a body lumen of a patient, comprising:
providing a medical device having a surface wherein said medical device comprises a needle;
suspending said medical device in an air stream, said air stream substantially devoid of suspending particles; and
coating at least a portion of said surface of said suspended medical device with a first coating material.

30. A method for coating at least a portion of a medical device for placement into a body lumen of a patient, comprising:
providing a medical device having a surface wherein said medical device comprises a blood filter;
suspending said medical device in an air stream, said air stream substantially devoid of suspending particles; and
coating at least a portion of said surface of said suspended medical device with a first coating material.

31. A method for coating at least a portion of a medical device for placement into a body lumen of a patient, comprising:
providing a medical device having a surface;
suspending said medical device in an air stream, said air stream substantially devoid of suspending particles; and
coating at least a portion of said surface of said suspended medical device with a first coating material;
wherein said method is conducted in a fluid bed chamber.

32. The method of claim 31 wherein said chamber comprises:
a structure having at least one side wall, a top opening, and a bottom opening;
an air distribution plate within said structure and secured to said side wall at a location between said top and bottom openings of said structure; wherein said air distribution plate has openings therein to allow a passage of air therethrough, said openings being smaller than said medical device; and
said air distribution plate defines a coating region above said air distribution plate within said structure.

33. The method of claim 32 wherein said structure is cylindrical.

34. The method of claim 32 wherein said air distribution plate has an open area of about 4 to about 30 percent.

35. The method of claim 32 wherein said air distribution plate comprises a metal screen of about 60 to about 325 mesh.

36. The method of claim 32 wherein said air distribution plate comprises a stationary perforated metal or ceramic plate.

37. The method of claim 32 wherein said air distribution plate comprises a rotatable perforated metal or ceramic plate.

38. The method of claim 32 wherein said air stream passes through said air distribution plate into said coating region.

39. The method of claim 32 wherein said chamber further comprises:
a tubular partition within said coating region, said tubular partition having a longitudinal axis substantially concentric with a longitudinal axis of said structure;
a nozzle positioned beneath said tubular partition substantially along said longitudinal axis of said structure and extending into said coating region, said nozzle injecting said air stream into said tubular partition; and
a second air stream passing through said air distribution plate into said coating region.

40. The method of claim 32 wherein a velocity of said first air stream is greater than a velocity of said second air stream.

41. The method of claim 40 wherein when said medical device is in said chamber, said first air stream pushes said medical device upward through said tubular partition, and said medical device falls downward outside of said tubular partition and through said second air stream.

42. A method for coating at least a portion of a medical device for placement into a body lumen of a patient, comprising:
providing a medical device having a surface;
suspending said medical device in an air stream, said air stream substantially devoid of suspending particles; and
coating at least a portion of said surface of said suspended medical device with a first coating material, wherein said first coating material includes a powder or solid without a solvent.

43. A method for coating at least a portion of a medical device for placement into a body lumen of a patient, comprising:
providing a medical device having a surface wherein said medical device comprises a stent;
suspending said medical device in an air stream, said air stream substantially devoid of suspending particles; and
coating at least a portion of said surface of said suspended medical device with a first coating material, wherein said first coating material comprises a therapeutic agent.

44. A method for coating at least a portion of a medical device for placement into a body lumen of a patient, comprising:
providing a medical device having a surface wherein said medical device comprises a stent;
suspending said medical device in an air stream, said air stream substantially devoid of suspending particles; and
coating at least a portion of said surface of said suspended medical device with a first coating material, wherein said first coating material comprises a therapeutic agent and a polymer.

* * * * *